(12) United States Patent
Jackson et al.

(10) Patent No.: US 6,814,722 B2
(45) Date of Patent: Nov. 9, 2004

(54) PRE-EXPANDED TAMPON PLEDGET

(75) Inventors: Dane R. Jackson, Bloomingdale, NJ (US); Karla E. Williams, Westwood, NJ (US); Suzanne Pauley, Charlotte, NC (US); Jeffrey Brown, Charlotte, NC (US)

(73) Assignee: Playtex Products, Inc., Westport, CT (US)

( * ) Notice: Subject to any disclaimer, the term of this patent is extended or adjusted under 35 U.S.C. 154(b) by 52 days.

(21) Appl. No.: 10/007,433

(22) Filed: Dec. 3, 2001

(65) Prior Publication Data

US 2002/0128620 A1 Sep. 12, 2002

Related U.S. Application Data

(63) Continuation-in-part of application No. 09/519,096, filed on Mar. 6, 2000, now abandoned.

(51) Int. Cl.[7] .............................................. A61F 13/20
(52) U.S. Cl. ................................. 604/385.17; 604/904
(58) Field of Search .......................... 604/904, 385.17, 604/385.18, 385.01

(56) References Cited

U.S. PATENT DOCUMENTS

| | | |
|---|---|---|
| 1,914,717 A | 6/1933 | Heuer |
| 1,964,911 A | 7/1934 | Haas ........................... 128/285 |
| 2,815,756 A | 12/1957 | Graham et al. ............. 128/285 |
| 2,934,068 A | 4/1960 | Graham et al. ............. 128/263 |
| 3,058,468 A | 10/1962 | Griswold et al. ........... 128/285 |
| 3,063,453 A | 11/1962 | Brecht ........................ 128/285 |
| 3,320,956 A | 5/1967 | Steiger ....................... 128/263 |
| 3,341,910 A | 9/1967 | Hesselholt |
| 3,431,909 A | 3/1969 | Krusko ....................... 128/285 |
| 3,593,715 A | 7/1971 | Merrill ....................... 128/285 |
| 3,738,364 A | 6/1973 | Brien et al. ................. 128/285 |
| 3,981,305 A | 9/1976 | Ring ........................... 128/285 |
| 4,300,561 A | 11/1981 | Kaczmarzyk et al. ....... 128/285 |
| 4,335,721 A | 6/1982 | Matthews ................... 128/285 |
| 4,374,522 A | 2/1983 | Olevsky ..................... 128/285 |
| 4,543,098 A | 9/1985 | Wolfe et al. ................ 604/370 |
| 4,627,849 A | 12/1986 | Walton et al. .............. 604/379 |
| 4,787,895 A | 11/1988 | Stokes et al. ............... 604/358 |
| 5,004,467 A | 4/1991 | Hinzmann et al. .......... 604/904 |
| 5,153,971 A | 10/1992 | Van Iten ....................... 28/118 |
| 5,350,371 A | 9/1994 | Van Iten ..................... 604/398 |
| 5,364,383 A | 11/1994 | Hayes et al. ................ 604/384 |

Primary Examiner—John J. Calvert
Assistant Examiner—Michele Kidwell
(74) Attorney, Agent, or Firm—Ohlandt, Greeley, Ruggiero, & Perle, LLP

(57) ABSTRACT

The present invention provides a pre-expanded tampon pledget formed from cellulosic absorbent fibers. The fibers are not tightly compressed, thus, the pledget has a reduced fiber density. As a result, a softer, more pliable pledget is formed that not only increases user comfort during use, but also affords a user with comparable and/or increased leakage protection over conventional tampons or tampon pledgets.

11 Claims, 1 Drawing Sheet

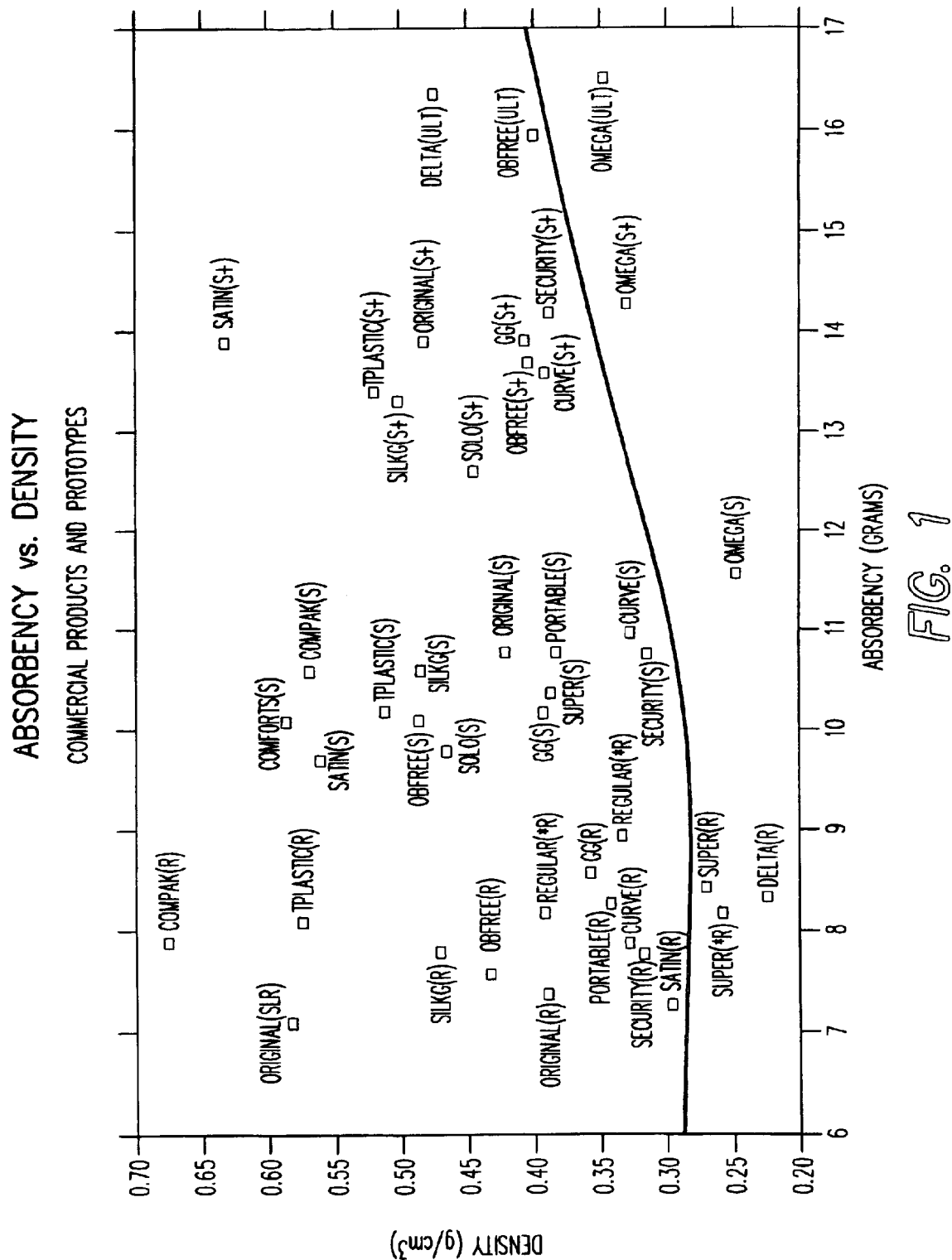

PRE-EXPANDED TAMPON PLEDGET

RELATED APPLICATION

This application is a continuation-in-part of U.S. application Ser. No. 09/519,096 filed on Mar. 6, 2000, now abandoned.

BACKGROUND OF THE INVENTION

1. Field of the Invention

The present invention relates generally to an improved tampon or tampon pledget. More particularly, the present invention relates to a pre-expanded tampon pledget. The pre-expanded tampon pledget has a reduced fiber density, yet provides comparable or improved leakage protection and performance compared to similar commercial compressed tampon pledgets.

Tampon pledgets are typically compressed either during manufacture or prior to placement in a tampon applicator. These tampon pledgets normally have their fibers compressed to enable easy ejection of the tampon pledget from the applicator and, more importantly, easy insertion of the tampon pledget in the vagina. In such a tampon pledget, the pledget's fibers will expand significantly upon initial contact with moisture. Once expanded, the tampon pledget will eventually conform to the body's contours to provide leakage protection. Conventionally, more fibers have been included in tampon pledgets, thereby increasing density (fibers per unit volume), in order to achieve better leakage protection. Such an increase in fibers normally results in a more tightly compressed, harder tampon pledget, which may cause user discomfort during insertion into the vagina.

U.S. Pat. No. 4,543,098 to Wolfe et al. discloses a multi-layered tampon pledget. The outer or transfer layer of the pledget is made from a web having thermoplastic fibers, which is integrated with a nonwoven thermoplastic fibrous cover. The inner layer includes a thermoplastic fiber such as one made from polyester, polypropylene, acrylic, nylon fibers or blends. The inner layer may optionally contain a non-thermoplastic fiber such as rayon, superabsorbent rayon, cellulosic fiber or blends of these fibers. Wolfe discloses that the density of the multi-layered pledget is preferred to be between about 0.15 and 0.25 g/cc. Wolfe also discloses that the absorbency for the multi-layered pledget is approximately 4 grams absorbed per gram weight of absorbent. Generally, the pledget itself weighs about 2.7 grams and it is preferred that at least 15% of the pledget weight is microfiber. Wolfe discloses that at levels below 15%, the pledget acts more like a sponge than a tampon.

Heretofore, there has been a lack of appreciation of the benefits of providing a tampon pledget that is less dense and, thus, has fewer fibers per unit volume. In addition, there has been a lack of appreciation that lower density or fewer fibers per unit volume achieves comparable and/or improved leakage protection over conventional tampon pledgets.

SUMMARY OF THE INVENTION

It is an object of the present invention to provide a tampon pledget with a reduced fiber density.

It is another object of the present invention to provide such a pledget that is pre-expanded, prior to its use.

It is still another object of the present invention to provide such a tampon pledget with improved leakage protection.

It is a further object of the present invention to provide such a pre-expanded pledget formed from cellulosic fiber.

It is still a further object of the present invention to provide such a tampon pledget that is softer and more comfortable during use.

It is yet a further object of the present invention to provide such a tampon pledget having increased cost benefits as a result of a reduction in fiber used to form the pledget.

Accordingly, the present invention provides a pre-expanded tampon pledget formed from cellulosic absorbent fibers. The fibers are not tightly compressed, thus, the pledget has a reduced fiber density. As a result, a softer, more pliable pledget is formed that not only increases user comfort during use, but also affords a user with comparable and/or increased leakage protection over conventional tampons or tampon pledgets.

BRIEF DESCRIPTION OF THE DRAWING

FIG. 1 is a graphical representation of absorbency versus density for both the pre-expanded tampon pledgets of the present invention and prior art commercial tampon pledgets.

DESCRIPTION OF THE INVENTION

The tampon pledget of the present invention is called a pre-expanded tampon pledget. As used in this application, pre-expanded means that the tampon or tampon pledget in its initial condition, such as just prior to use, has an expanded or larger diameter and volume, yet it has a reduced fiber density. However, when fully expanded after absorption of fluid, the pre-expanded tampon pledget has about the same diameter as a conventional tampon pledget.

The pre-expanded pledget of the present invention is formed from cellulosic fibers. Conventional cellulosic fibers can be used. Such suitable cellulosic fibers include, for example, rayon, cotton, pulp, or any combinations thereof. Preferably, the rayon fiber has a denier of about 1.1 to about 3.

The pre-expanded pledget of the present invention has an absorbency between about 6 grams to about 18 grams, as tested per the Federal Register §801.430. More specifically, absorbencies can be further defined pursuant to federal regulations as follows:

| | |
|---|---|
| Regular | 6 to 9 grams of absorbency; |
| Super | 9 to 12 grams of absorbency; |
| Super Plus | 12 to 15 grams of absorbency; |
| Ultra | 15 to 18 grams of absorbency. |

The pre-expanded tampon pledget of the present invention can be crimped or compressed to a certain extent. However, the pre-expanded tampon pledget of the present invention has a diameter in its initial condition from about 0.5 inches to about 1.75 inches varying with the absorbency range of the pre-expanded pledget.

By enlarging the diameter of the pre-expanded pledget of the present invention, while maintaining the same amount of fiber, the tampon pledget is less dense. The lower density, in turn, provides for more efficient fiber absorbency, thus allowing the use of less fiber. The amount or weight of cellulosic fiber used in the pledget is reduced over conventional tampons or tampon pledgets, as those set forth in FIG. 1 herein. The pre-expanded pledget has about 1.1 grams to about 4.5 grams of cellulosic fibers, which essentially amounts to the total weight of the pledget. The amount of fibers present varies with the absorbency range of the pledget.

The pre-expanded pledget of the present invention has a volume about 8 cubic centimeters (cc) to about 60 cc, varying with the absorbency range of the pledget. The increased volume is due to the increased diameter of the pledget, as set forth above. It has been determined that the volume of the pre-expanded pledget must be sufficiently increased, otherwise, there is substantially no improvement or increase in leakage protection observed.

To maximize its benefits, the pre-expanded tampon pledget of the present invention has a reduction in fiber density. The pre-expanded pledget has a density from about 0.01 g/cc to about 0.39 g/cc, varying with the absorbency range of the pledget. In addition, the cellulosic fiber present in the pre-expanded pledget is much less compressed than the fiber in conventional tampon pledgets. Preferably, the fiber in the pre-expanded tampon pledget may be as much as about three times less compressed than the fiber in conventional tampon pledgets. Despite the much lower fiber density, as well as less compression, the pre-expanded tampon pledget unexpectedly provides increased protection against leakage.

In addition, the reduced fiber density in the pre-expanded pledget of the present invention creates larger pathways/pores for the fluid to enter and move through the tampon. This eliminates the need for any transfer layer, which leads to further cost savings and manufacturing efficiencies.

The pre-expanded tampon pledget of the present invention is also softer and more flexible due to the lower fiber density. Accordingly, the pre-expanded tampon pledget affords a user increased comfort during insertion and during wear. Also, the initial, pre-expanded condition of the tampon pledget of the present invention can make the pledget conform more quickly to the user's anatomy since less moisture is needed to contact the pledget to cause the expansion.

An important aspect of the present invention is that the pre-expanded pledget is formed from conventional cellulosic fibers, and therefore, can be constructed using conventional methods and equipment known in the art. Suitable methods of construction include, for example, cross-pad, flat pad, or rolled/radial construction.

In one preferred embodiment of the present invention, the pre-expanded pledget has an absorbency about 6 to about 9 grams. Preferably, the diameter of the pledget in this absorbency range, in its initial condition, is about 0.5 inches to about 0.8 inches. More preferably, the diameter is about 0.6 inches to about 0.7 inches.

The pre-expanded pledget in this absorbency range has cellulosic fiber in an amount about 1.6 grams to about 2.4 grams. Preferably, to improve the benefits of the pre-expanded pledget, the fiber is present in an amount about 1.85 grams to about 2.15 grams. The pre-expanded pledget of this embodiment has a volume of about 7 cc to about 12 cc. More preferably, the volume is about 8 cc to about 11 cc.

The pre-expanded pledget of this embodiment has a density about 0.01 g/cc to about 0.31 g/cc. Preferably, the density is about 0.15 g/cc to about 0.29 g/cc. More preferably, the density of the pre-expanded tampon pledget is about 0.17 to about 0.25 g/cc.

In another preferred embodiment of the present invention, the pre-expanded pledget has an absorbency between about 9 to about 12 grams. Preferably, the diameter of the pledget in this absorbency range, in its initial condition, is about 0.65 inches to about 0.8 inches. More preferably, the diameter is about 0.7 to about 0.75 inches.

The pre-expanded pledget in this absorbency range has cellulosic fiber in an amount about 2.25 grams to about 2.75 grams. Preferably, to improve the benefits of the pre-expanded pledget, the fiber is present in an amount about 2.4 grams to about 2.6 grams. The pre-expanded pledget of this embodiment has a volume about 9 cc to about 14 cc. More preferably, the volume is about 9 cc to about 11 cc.

The pre-expanded pledget of this embodiment has a density about 0.01 g/cc to about 0.32 g/cc. Preferably, the density is about 0.15 g/cc to about 0.30 g/cc. More preferably, the density of the pre-expanded tampon pledget is about 0.17 to about 0.25 g/cc.

In another preferred embodiment of the present invention, the pre-expanded pledget has an absorbency between about 9 to about 12 grams. Preferably, the diameter of the pledget, in its initial condition, is about 1.25 inches to about 1.75 inches. More preferably, the diameter is about 1.4 to about 1.6 inches.

This pre-expanded pledget has cellulosic fiber in an amount about 1.1 grams to about 1.7 grams. Preferably, to improve the benefits of the pre-expanded pledget, the fiber is present in an amount about 1.3 grams to about 1.5 grams.

The pre-expanded pledget of the present invention has a volume about 40 cc to about 60 cc. More preferably, the volume is about 45 cc to about 55 cc.

The pre-expanded pledget of this embodiment has a density about 0.01 g/cc to about 0.05 g/cc. Preferably, the density of the pre-expanded tampon pledget is about 0.02 to about 0.035 g/cc.

In another preferred embodiment of the present invention, the pre-expanded pledget has an absorbency about 12 to about 15 grams. Preferably, the diameter of the pledget in this absorbency range, in its initial condition, is about 0.65 inches to about 0.8 inches. More preferably, the diameter is about 0.7 to about 0.75 inches.

The pre-expanded pledget in this absorbency range has cellulosic fiber in an amount about 3 grams to about 3.5 grams. Preferably, to improve the benefits of the pre-expanded pledget, the fiber is present in an amount about 3.15 grams to about 3.25 grams.

The pre-expanded pledget of this embodiment has a volume about 10 cc to about 15 cc. More preferably, the volume is about 11 cc to about 13 cc.

The pre-expanded pledget of this embodiment has a density about 0.01 g/cc to about 0.35 g/cc. Preferably, the density is about 0.20 g/cc to about 0.33 g/cc. More preferably, the density of the pre-expanded tampon pledget is about 0.24 to about 0.30 g/cc.

In another preferred embodiment of the present invention, the pre-expanded pledget has an absorbency between about 15 to about 18 grams. Preferably, the diameter of the pledget in this absorbency range is about 0.65 inches to about 0.8 inches. More preferably, the diameter is about 0.7 to about 0.75 inches.

The pre-expanded pledget in this absorbency range has non-thermoplastic fiber in an amount about 3.5 grams to about 4.5grams. Preferably, to improve the benefits of the pre-expanded pledget, the fiber is present in an amount about 3.8 grams to about 4.2 grams.

The pre-expanded pledget of the present invention has a volume about 10 cc to about 15 cc. More preferably, the volume is about 11 cc to about 13 cc.

The pre-expanded pledget of this embodiment has a density about 0.01 g/cc to about 0.39 g/cc. Preferably, the density is about 0.25 g/cc to about 0.35 g/cc. More preferably, the density of the pre-expanded tampon pledget is about 0.30 g/cc to about 0.35 g/cc.

In short, by enlarging the tampon pledget's diameter (pre-expanded) and reducing the amount of fiber present in the pre-expanded pledget, the density is greatly decreased, yet leakage protection is unexpectedly improved.

Another important aspect of the present invention is that the above-described pre-expanded pledget and all described properties are achieved without the use of thermoplastic and/or synthetic fibers, without the effect of a transfer layer, and without the effect of a coverstock. This attributes to the reduced cost and ease associated with making the pre-expanded pledget of the present invention since conventional cellulosic fibers and methods of construction can be employed.

While not necessary, the pre-expanded pledget can be used with a coverstock. The coverstock can be any conventional coverstock. By way of example, the coverstock can be made of mono- or multi-component fibers of polyester, polypropylene, polyethylene, or any combinations thereof. The density of the coverstock will be approximately 0.3 g/cc. Also, the coverstock can entirely cover or partially cover the tampon pledget. However, the coverstock should not impinge upon the pre-expanded state of the tampon pledget.

In addition, the pre-expanded pledget can also include synthetic or thermoplastic based fibers. These fibers may be, for example, mixed or layered with the non-thermoplastic fibers described above so as to impart some resiliency and/or wet collapse resistance. These thermoplastic fibers form a matrix/lattice, which hold and separate the absorbent, non-thermoplastic fibers so as to provide a substantial wet environment support. These fibers can be of any type known in the art as long as the fibers do not significantly decrease in modulus when wet or hinder the absorption of fluid to the absorbent cellulosic fibers. Suitable fibers include, for example, polyester, polypropylene, polyethylene, acrylic, nylon, polyurethane, polyvinyl, acetate, glass, or any combinations thereof. These fibers have a denier between about 1.1 to about 30, and more preferably 6 to 15 denier.

Tests have demonstrated the performance of the tampon pledget made in accordance with the present invention. The graph shown in FIG. 1 illustrates a syngyna test of commercial tampons versus the pre-expanded tampon pledgets of the present invention of various diameters.

The several more preferred embodiments of pre-expanded tampon pledgets of the present invention are designated as Delta Regular (R), Super Regular (R), Omega Super (S), PNT Super (S), Super Plus (S+), and Omega Ultra (ULT). These pledgets have the following properties:

| Tampon Pledget | Fiber Weight (g) | Diameter (inches) | Length (inches) | Volume (cc) | Density (g/cc) |
| --- | --- | --- | --- | --- | --- |
| Delta Regular | 1.9 | 0.67 | 1.75 | 10.1 | 0.185 |
| Super Regular | 2.05 | 0.62 | 1.75 | 8.7 | 0.237 |
| PNT Super | 1.4 | 1.5 | 1.75 | 50.7 | 0.028 |
| Omega Super | 2.50 | 0.73 | 1.75 | 12.0 | 0.208 |
| Omega Super Plus | 3.15 | 0.73 | 1.75 | 12.0 | 0.262 |
| Omega Ultra | 3.95 | 0.73 | 1.75 | 12.0 | 0.329 |

The commercial products tested include three Regular (R), Super (S) and Super Plus (S+) for products under the following trademarks/names: Compak, Satin Touch, Comfort Shape, Plastic, Originals, and Solos, all of which are sold by Tampax; Silk Glide, Gentile Glide, Portables, and experimental designs, such as, Regular (*R), Super (S), and Delta (ULT), all of which are distributed by Playtex Products, Inc.; OB Free Regular (R), Super (S), Super Plus (S+), and Ultra (ULT), all four of which are sold by Personal Products Company; and Kotex Security Regular (R), Super (S) and Super Plus (S+), all three of which are sold by Kimberly Clark Corp. It should be noted that all Personal Products Company, Kimberly Clark Corp. and Playtex Products, Inc. Silk Glides products have coverstocks. However, the coverstocks should not effect the data provided above.

FIG. 1 is a plot of density versus absorbency. The density numbers are dry numbers. As shown in the plot, the pre-expanded tampon pledgets of the present invention have a reduced density compared to those commercial tampons tested in their respective absorbency ranges. Thus, the improved absorbency, despite a reduced density, of the pre-expanded pledgets of the present invention is further illustrated.

As a result, a softer, more pliable pledget is formed that not only increases user comfort during use, but also affords a user with comparable and/or increased leakage protection over conventional tampons or tampon pledgets.

Various modifications may be made as will be apparent to those skilled in the art. Thus, it will be obvious to one of ordinary skill in the art that the foregoing description is merely illustrative of certain preferred embodiments of the present invention, and that various obvious modifications can be made to these embodiments.

What is claimed is:

1. A pre-expanded tampon pledget having a density of about 0.02 g/cc to about 0.035 g/cc and an absorbency of about 9 grams to about 12 grams.

2. The pre-expanded pledget of claim 1, wherein the tampon pledget comprises a cellulosic fiber.

3. The pre-expanded tampon pledget of claim 2, wherein said cellulosic fiber is selected from the group consisting of rayon, cotton, pulp, and any combinations thereof.

4. The pre-expanded tampon pledget of claim 2, wherein said cellulosic fiber is present in the tampon pledget in an amount about 1.1 grams to about 1.7 grams.

5. The pre-expanded tampon pledget of claim 1, wherein said absorbency is achieved without the use of a transfer layer.

6. The pre-expanded tampon pledget of claim 1, wherein the tampon pledget has a volume about 40 cc to about 60 cc.

7. The pre-expanded tampon pledget of claim 1, wherein the tampon pledget has a diameter in an initial condition about 1.25 inches to about 1.75 inches.

8. The pre-expanded tampon pledget of claim 1, wherein the tampon pledget has a cross-pad construction.

9. The pre-expanded tampon pledget of claim 1, wherein the tampon pledget has a radial construction.

10. The pre-expanded tampon pledget of claim 1, wherein the tampon pledget has a flat pad construction.

11. The pre-expanded tampon pledget of claim 1, further comprising a coverstock about at least a portion of the tampon pledget.

* * * * *